(12) United States Patent
Prado et al.

(10) Patent No.: US 9,261,470 B2
(45) Date of Patent: Feb. 16, 2016

(54) HIGH PRECISION ELEMENTAL COMPOSITION DETERMINATION

(71) Applicant: One Resonance Sensors, LLC, San Diego, CA (US)

(72) Inventors: Pablo Prado, San Diego, CA (US); Andrew McDowell, Albuquerque, NM (US); James Chepin, San Diego, CA (US)

(73) Assignee: ONE RESONANCE SENSORS, LLC, San Diego, CA (US)

( * ) Notice: Subject to any disclaimer, the term of this patent is extended or adjusted under 35 U.S.C. 154(b) by 0 days.

(21) Appl. No.: 14/201,340

(22) Filed: Mar. 7, 2014

(65) Prior Publication Data
US 2015/0253264 A1    Sep. 10, 2015

(51) Int. Cl.
| G01V 3/00 | (2006.01) |
| G01N 24/08 | (2006.01) |
| G01R 33/28 | (2006.01) |
| G01R 33/58 | (2006.01) |
| G01R 33/36 | (2006.01) |

(52) U.S. Cl.
CPC .............. *G01N 24/082* (2013.01); *G01R 33/28* (2013.01); *G01R 33/3642* (2013.01); *G01R 33/583* (2013.01)

(58) Field of Classification Search
CPC .................................................... G01R 33/583
USPC .......................... 324/314, 303, 322, 318, 300
See application file for complete search history.

(56) References Cited

U.S. PATENT DOCUMENTS

| 4,684,895 A | 8/1987 | Misic |
| 4,739,268 A * | 4/1988 | Fox ............................. 324/314 |
| 5,451,873 A * | 9/1995 | Freedman et al. ............ 324/303 |
| 5,500,591 A | 3/1996 | Smith et al. |
| 5,698,979 A | 12/1997 | Taicher et al. |
| 6,054,858 A * | 4/2000 | Dumoulin et al. ............ 324/322 |
| 6,392,408 B1 | 5/2002 | Barrall et al. |
| 7,026,814 B2 * | 4/2006 | Bordon et al. ............... 324/303 |
| 7,355,402 B1 | 4/2008 | Taicher et al. |
| 7,759,938 B2 | 7/2010 | Prado et al. |
| 2010/0090698 A1 | 4/2010 | Blumich et al. |
| 2010/0141255 A1 | 6/2010 | Adolphi et al. |
| 2011/0018535 A1* | 1/2011 | Rudakov ...................... 324/303 |
| 2011/0109310 A1 | 5/2011 | Hornung |
| 2013/0200899 A1 | 8/2013 | Yi et al. |
| 2013/0234706 A1 | 9/2013 | Mandal et al. |

FOREIGN PATENT DOCUMENTS

WO       2013077922 A3    8/2013

OTHER PUBLICATIONS

International Search Report and Written Opinion received in PCT/US2015/019289, mailed May 29, 2015, 10 pages.
International Search Report and Written Opinion received in PCT/US2012/053575, dated May 13, 2013, 9 pages.

(Continued)

*Primary Examiner* — Louis Arana
(74) *Attorney, Agent, or Firm* — Procopio, Cory, Hargreaves & Savitch LLP (57) ABSTRACT

High precision elemental concentration determination is achieved using a nuclear magnetic resonance device that can continuously monitor samples of a source fluid in the field and in the refinery plant while the source fluid is refined into a desired product fluid.

20 Claims, 6 Drawing Sheets

(56) References Cited

OTHER PUBLICATIONS

First Saudi Arabian Office Action received in 114350371, 5 pages.
Extended European Search Report received in 12851906.3, dated Mar. 24, 2015, 10 pages.
Burnett et al. "Signal processing considerations in NMR detection of liquid explosives," Proceedings of SPIE, vol. 1824, Nov. 16, 1992, 11 pages.
Espy et al. "Progress on Detection of Liquid Explosives Using Ultra-Low Field MRI," IEEE Transactions on Applied Superconductivity, vol. 21, No. 3, Jun. 1, 2011, 4 pages.
Gradisek et al. "NMR-Based Liquid Explosives Detector," Applied Magnetic Resonance, vol. 38, No. 4, Jun. 18, 2010, 9 pages.
Gudmundson et al "Detection and Classification of Liquid Explosives Using NMR," Acoustics, Speech, and Signal Processing, Apr. 19, 2009, 4 pages.
King et al. "Development and evaluation of magnetic resonance technologies, particularly NMR, for detection of explosives," Applied Magnetic Resonance, vol. 25, No. 3-4, Sep. 1, 2004, 31 pages.
Kumar, "Liquid-contents verification for explosives, other hazards, and contraband by magnetic resonance," Applied Magnetic Resonance, vol. 25, No. 3-4, Sep. 1, 2004, 13 pages.
Kumar et al. "Screening sealed bottles for liquid explosives," Proceedings of SPIE, vol. 2934, Jan. 29, 1997, 12 pages.
Kumar et al. "Magnetic-resonance-based system for chemical agent screening," Proceedings of SPIE, vol. 5071, Sep. 23, 2003, 12 pages.
Mauler et al. "Identification of Liquids Encountered in Carry-on-Luggage by Mobile NMR," Explosives Detection Using Magnetic and Nuclear Resonance Techniques, 2009, 13 pages.

\* cited by examiner

HIGH PRECISION ELEMENTAL COMPOSITION DETERMINATION

CROSS-REFERENCE TO RELATED APPLICATIONS

The present application is related to U.S. patent application Ser. No. 14/201,222 filed on Mar. 7, 2014, which is hereby incorporated by reference in its entirety.

BACKGROUND

1. Field of the Invention

The present invention is generally directed toward nuclear magnetic resonance ("NMR") and is more particularly directed toward high precision elemental composition determination using NMR.

2. Related Art

Measurements of the concentration of various elements are valuable in a number of industrial situations. Examples include the characterization of the elemental content of raw materials or feedstocks, the monitoring of concentrations in various stages of material or chemical processing, the certification of elemental content of finished products, and the verification of product quality by downstream customers. The elemental concentration measurement usually needs to be cost effective, precise, rapid, robust, straightforward and flexible in order to provide maximal economic benefit. In some cases, the measurement must be minimally or non-invasive and non-destructive.

A number of analytical chemistry techniques are used for elemental analysis and concentration determination. Techniques based on inductively-coupled plasma sample decomposition, followed by detection with mass spectrometry, atomic emission spectroscopy, or other methods are common. Flame-based atomic emission spectroscopy or atomic absorption spectroscopy may also be used. Classical wet chemistry methods may be employed, including precipitation, titration, or other approaches. Separation techniques such as gas chromatography, liquid chromatography, or capillary electrophoresis may be employed. Nuclear magnetic resonance spectroscopy may also be utilized for certain elements.

The currently available solutions for measuring elemental concentration all fail to meet one or more of the requirements of cost, precision, speed, robustness, simplicity, and flexibility. For nearly all of them, the sample to be measured must be prepared carefully by a technician, usually in a wet chemistry laboratory. The accuracy relies heavily on multipoint calibration curves and may nevertheless be limited even under ideal measurement conditions. Complicated procedures limit the practically achievable measurement precision. Some techniques, such as conventional NMR, may be considered ill-suited for high precision determinations and may be used mostly for qualitative analysis. Some instruments or procedures may be limited to a single chemical element, or a small number of elements, when the need exists for multi-element characterization. The cost per measurement may be high due to capital equipment and siting expenses, the cost of consumables, maintenance costs, and the technician's time. The measurement procedure may take too much time to provide effective feedback to operational decisions and control. Similarly, the measurement facility may be too far removed from the operational facility to allow for effective integration of process and characterization. Variations between samples, or between technicians, may cause the measurements to fail to meet accuracy requirements. The devices and methods used may fail to meet the desired performance specifications under non-ideal factory or field conditions, or the devices may not be capable of being moved to or being operated in the locations where the measurements need to be made. This lack of flexibility, or the failure to meet other requirements of cost, precision, ease of use, measurement speed, integrability with other processes, and robustness can undermine the desired application of any of the currently available elemental concentration determination methods.

Therefore, what is needed is a system and method that overcomes these significant problems found in the conventional systems as described above.

SUMMARY

The invention disclosed herein overcomes these limitations by providing a new form of nuclear magnetic resonance apparatus and data analysis that is optimized to meet the requirements of practical elemental concentration measurements. The device is based on a small permanent magnet, allowing it to be low-cost, portable, and virtually maintenance free. The NMR-based detection allows the use of unprocessed sample fluids, minimizing sample handling and preparation. The NMR-based method also allows simple single-point calibration and very simple operation; minimal expertise and training is required, and inter-operator variation is reduced or eliminated. New NMR experiment control steps and data analysis methods disclosed herein provide levels of accuracy and precision above those of previous NMR methods. New NMR electronics capable of operating efficiently over a large range of frequencies without requiring switched circuit elements allows multi-element characterization with high precision. The permanent magnet platform produces an NMR device that is functional in non-laboratory environments and can be used to characterize samples at the time and place where this characterization is most desired; integration with normal industrial workflow and processes is possible.

The invention disclosed herein is based on NMR, as opposed to the more typical elemental analysis methods which utilize optical or mass spectroscopic approaches. Sample handling and preparation requirements are substantially less stringent for NMR than for the other techniques. The NMR method is non-destructive and the sample can be returned to the source, including in a flow-through configuration. The strength of the NMR signal is directly proportional to the concentration of the measured element, so that only a single-point calibration is needed, as opposed to the multi-point or non-linear calibration curves typical of other techniques. The calibration can be made independent of the fluid matrix or molecular structure of the element-containing fluid, which is often not possible for the other techniques. However, standard implementations of NMR for sample characterization are typically limited to a signal strength variability of 1% or larger, and it is difficult to detect signals from a sample with less than 1000 ppm concentration, by weight or number. (Industry prefers data in terms of weight percent, while the NMR data yield number concentration, which can be converted to weight percent using the weight of the element being measured.) The invention disclosed here differs from other NMR devices in that the data are acquired and analyzed in a way that achieves much higher precision and much lower limits of detection by sacrificing the spectral information that is normally the priority for NMR devices. Conventional NMR spectroscopy is optimized for determining molecular identity or structure, rather than concentration of elemental species. Furthermore, traditional NMR devices are expensive to buy and maintain, are lab bound and delicate, and are difficult to operate. The invention disclosed herein differs from these systems by being based on a permanent magnet, allowing the new device to be small, inexpensive, robust, and easy to operate.

Additional advantages of the device disclosed herein may be derived from the use of multiple such devices, for example in a network or in an over-arching process monitoring and/or control system. Likewise, properties of the device disclosed herein allow it to be used in a mobile or portable configuration, in stand-alone mode or with a constant or intermittent connection to a larger monitoring and/or control system.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for high precision elemental concentration determination using a nuclear magnetic resonance device. For example, one embodiment disclosed herein allows for a mining operation to continuously monitor samples of a source fluid in the field and in the refinery plant while the source fluid is refined into a desired product fluid. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
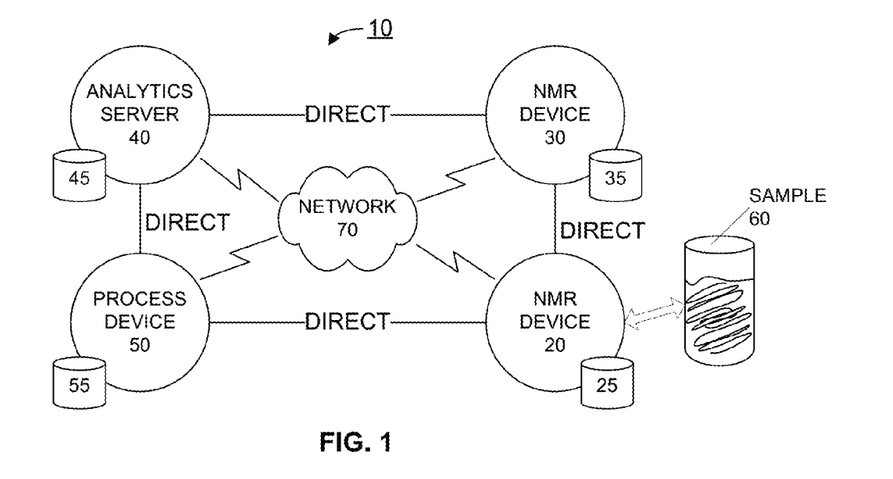
FIG. 1 is a network diagram illustrating an example system for high precision elemental composition determination according to an embodiment of the invention.

FIG. 1 is a network diagram illustrating an example system 10 for high precision elemental composition determination according to an embodiment of the invention. In the illustrated embodiment, the system 10 comprises one or more NMR devices 20 (and 30), one or more analytics servers 40 and one or more process devices 50. The various devices 20, 30, 40 and 50 each also comprise a non-transitory computer readable storage device, respectively 25, 35, 45 and 55. The system 10 may also include a network 70 through which the various devices 20, 30, 40 and 50 are communicatively coupled. The various devices 20, 30, 40 and 50 in the system 10 may also be directly connected (wired or wirelessly) to each other to facilitate communication amongst the various devices in the system 10. In one embodiment, a plurality of NMR devices 20 and 30 can be communicatively coupled directly or via network 70 or by some combination of direct and network connections.

The NMR device 20 is configured to determine the concentration of one or more elements in a sample 60. The NMR device 20 may store the determined concentration value in a local storage device 25 or it may communicate the determined value to other devices directly or via a network 50, or both. The NMR device 20 operates by exposing the sample 60 to a static magnetic field to align the nuclear spins of elements in the sample 60 whose concentration is to be determined. Once exposed to the static magnetic field, the sample 60 is subjected to one or more pulses of a stimulus magnetic field at the Larmor frequency determined by a combination of the nuclear gyromagnetic ratio and the applied static magnetic field. Finally, the NMR device 20 detects and quantifies an electrical signal corresponding to a responsive magnetic field emitted by the sample 60 as the nuclear spins precess in response to the applied pulses of the stimulus magnetic field.

Analytics server 40 is configured to receive information from devices, including for example, one or more NMR devices 20 and/or one or more process devices 50 and utilize this information, together with other information it may receive or may have previously stored, to perform an analysis. The results of this analysis may be stored in memory unit 45, and/or be used to send information or control signals to other devices in the network, including for example one or more NMR devices 20 and/or one or more process devices 50.

Process device 50 is configured to perform one or more steps in an industrial or research process, including chemical or mechanical processing of materials such as mining materials and fluids. The one or more process devices 50 may be configured so that they receive inputs or control signals from one or more NMR devices 20, directly or via a network 70, and they may additionally or alternatively receive such inputs and signals from one or more analytics servers 40.

In one embodiment, the sample 60 may be, for example, a fluid containing elements of commercial interest at any stage of the extraction and refining process, e.g., raw fluid coming from a drilling operation or operating well; fluids stored or processed or partially processed in the field; and fluid during refining to extract the desired element, just to name a few. The fluid can be brought from the source to NMR device 20 by various means, for example in sealed vials or in a continuous-flow tube representing, for example, the main process fluid conduit, or a side channel of the extraction or refining process, controlled by valves. The NMR device 20 determines the concentration of the element of interest in the tube and stores the result in memory 25, as well as optionally sending the information to analytics server 40 and its memory unit 45 via network 70 or a direct wired or wireless connection.

Network 70 may be a wired or wireless network, packet or switched network, public or private network, or any combination of these. In an embodiment where NMR device 20 is taken into the field (e.g., a remote a lake or reservoir, a remote wellhead or remote drill head), the network 70 may include an intermittent connection with the NMR device 20 so that the NMR device 20 may reconnect to the network 70 when it is returned from the remote location. Network 70 can also include a wireless communication network so that devices in the field can remain communicatively coupled to the other devices in the system 10.

In one embodiment, NMR device 20 may be used to control process device 50. For example, the output of NMR device 20 may be used to direct the continuation or cessation of the drilling of an exploratory well in search of a fluid, such as a brine, containing an element of interest, where said drilling operation is wholly or partially controlled by process device 50. In another example, the degree of extraction in successive stages of a refining process that extracts the element of interest from a fluid can be monitored (and in one embodiment, controlled) by NMR device 20.

In one embodiment, analytics server 40 can also control process device 50. For example, analytics server 40 may implement a decision or calculation algorithm that takes as inputs the information from one or more NMR devices 20 and produces as outputs control signals for one or more process devices 50. Such control signals may be digital or analog voltages, for example. The analytics server 40 may send the control signals directly to the process device 50 to be controlled, or may send such signals indirectly to the process device 50 via one or more intermediate devices, for example, one or more NMR devices 20.

In practice, NMR device 20 can be used in a variety of ways, including but not limited to, for example: (a) being used in a portable, autonomous (non-networked) manner simply to measure samples of interest; (b) being used autonomously for data collection, with later reconnection with a network for transmission/transfer of data that was stored/logged during data collection so that such collected data can be analyzed and used for decision-making; (c) for comparison of samples at different times at the same stage of a process; (d) for comparison of samples at different points along a process; (e) for quality control or acceptance testing (comparison against a fixed or reset standard); (f) for direct control of a process, including changes to preceding or subsequent process variables, or as a gateway for entry into later processes.

Figure 2:
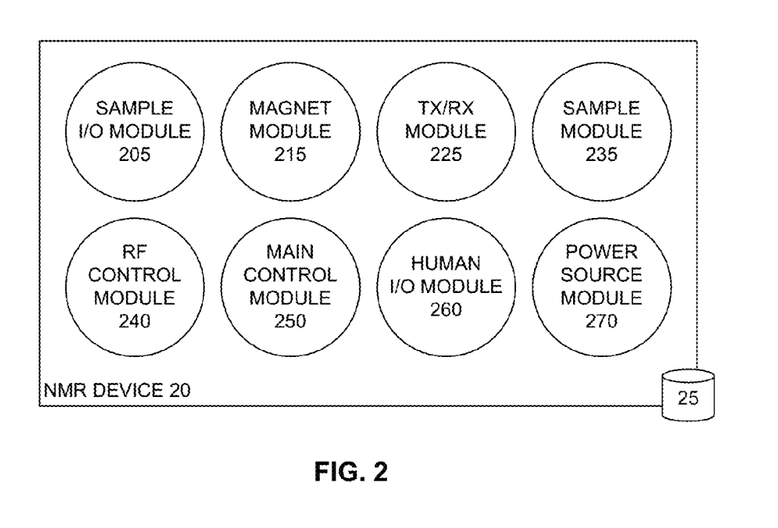
FIG. 2 is a block diagram illustrating an example nuclear magnetic resonance device according to an embodiment of the invention.

FIG. 2 is a block diagram illustrating an example nuclear magnetic resonance device 20 with its data storage device 25, according to an embodiment of the invention. In the illustrated embodiment, the NMR device 20 comprises a sample I/O module 205, a magnet module 215, a transmit/receive ("Tx/Rx") module 225, a sample module 235, an RF control module 240, a main control module 250, a human I/O module 260 and a power source module 270. As previously discussed, the NMR device 20 also comprises a non-transitory computer readable storage device 25.

The sample I/O module 205 is configured to introduce to, support, and remove samples from the NMR device 20. The sample I/O module 205 is designed to introduce the sample reproducibly into the sample module 235 where the sample can be supported and is therefore compatible with the hardware of sample module 235. Sample I/O module 205 may include a removable glass or plastic tube sealed on one end or alternatively sealed at both ends. Sample I/O module 205 may also include flow-through tubing with one or more downstream and/or upstream valves to control the entry of sample fluid into the sample I/O module 205. The flow-through tubing advantageously allows for continuous or near-continuous sampling of a fluid in a process flow. The flow-through tubing may be replaceable or non-replaceable.

Sample I/O module 205 may also incorporate manifolds and associated valves to enable selection between a sample, calibration fluids, and cleaning fluids or gases. Sample I/O module 205 may also include hardware to allow sealed sample tubes to be inserted from one direction and removed from the other direction. Additionally, the Sample I/O module 205 may also include hardware such as filters, frits, and back-flushing means to keep the sample area clean and unclogged. Other options and attachments for the sample I/O module 205 may also be included as will be understood by those skilled in the art.

The magnet module 215 is configured to produce a substantially spatially uniform static magnetic field surrounding and permeating the sample during the measurement. The magnetic module 215 may also be configured to regulate the temperature of the constituent parts of the magnet module. In addition, the magnet module may also be configured so as to regulate the temperature of other modules inserted into the magnet module, for example the sample module 235 or the sample I/O module 205, or portions of such modules as may be inserted into the magnet module.

The magnet module 215 comprises permanent magnet materials that are used to generate the static magnetic field. Alternatively, an electromagnet or a superconducting magnet may be used. The magnet module may utilize pole pieces arranged on either side of a gap or opening in which the sample is located. Alternatively, the magnet module may utilize magnetic field sources of particular strengths arranged at locations and orientations (such as in a Halbach array configuration) surrounding the sample opening in a way appropriate for creating a magnetic field in that opening.

Since the NMR frequency of a given element is the product of its gyromagnetic ratio and the applied magnetic field, it is important that the static magnetic field be relatively uniform throughout the sample measurement volume (e.g., the sample I/O area in which the sample is supported during measurement). For example, a uniformity of the field strength to within approximately 0.01% (one part in ten thousand) or better may be desired. This may be accomplished via field shaping materials applied to the magnet poles and adjusted until the target uniformity is achieved. Alternatively, the desired field homogeneity may be achieved by adjusting positions of some or all of the pieces comprising the magnet module 215. Flux return materials such as iron or soft steel may be used to link the magnet poles in the regions of space not being utilized for generation of the NMR polarizing field. The magnet module 215 may optionally include mechanically adjustable elements to allow post-fabrication adjustment of the NMR polarizing field and its uniformity.

The strength of the static magnetic field produced by the magnet module 215 depends on temperature, so the NMR frequency is temperature dependent. In one embodiment, special materials (except perhaps thermal insulation), structures, or cooling methods are not utilized to regulate the temperature of the magnet module 215. Advantageously, excluding such cooling materials, structures and methods reduces the variation in the strength of the magnetic field produced by the magnet module 215 and consequently results in a more uniform magnetic field, which is highly desirable. Alternatively, the magnet module 215 may contain technologies that reduce or eliminate the temperature dependence of the NMR frequency. Such technologies may include: active thermal stabilization, special permanent magnetic materials with reduced or inverted temperature coefficients, structural materials chosen for their particular (often low) value of thermal expansion coefficient, temperature-dependent flux-shunting materials sized and located to compensate for the temperature dependence of the other components of the magnet module 215, electrical current coils arranged and controlled to create a magnetic field contribution that cancels that due to the temperature dependence of other components, or any other methods for field stabilization known in the art.

The magnet module 215 may also be surrounded by magnetically permeable materials that both reduce the effect of ambient, external magnetic field variations on the NMR field and reduce the presence of stray magnetic fields outside the measurement volume.

The Tx/Rx module 225 is configured to provide electric current that, in conjunction with a coil in the sample module 235, excite target elements with magnetic stimulus fields. Specifically, the Tx/Rx module 225 generates current and applies the current to the sample module 235, which in turn generates a magnetic field at the resonance frequency at which the target element is excited. In one embodiment, the Tx/Rx module 225 generates and applies current to the sample module in pulse sequences. The sample module 235 includes at least one coil, which receives the current in pulse sequences from the Tx/Rx module 225 and emits corresponding pulse sequences of magnetic field stimulus at the desired resonance frequency (e.g., the frequency at which the target element is excited). Advantageously, the current pulses induce a magnetic field in proportion to the inductance of the coil in the sample module 235 at the desired frequency.

The Tx/Rx module 225 is also configured to generate electrical signals corresponding to responsive magnetic fields emitted from the target elements in the sample under interrogation in response to the pulse sequences of stimulus magnetic field. Specifically, after excitation by the stimulus magnetic field, the target element emits a responsive magnetic field into a coil of the sample module 235 at a frequency characteristic of the NMR properties of the target element. The coil in the sample module 235 that detects the responsive magnetic field may be the same coil that generated the stimulus magnetic field as described above, according to one embodiment. In an alternative embodiment, the coil that detects the responsive magnetic field may be a receiver coil, different from an excitation coil that produces the stimulus magnetic field. In response to the presence of the responsive magnetic field from the target element, the receiver coil of the sample module 235 generates a voltage and the Tx/Rx module 225 senses this voltage in the receiver coil and generates an electrical signal that corresponds to the target element. The NMR signal is provided to and/or received by the RF control module 240.

The Tx/Rx module 225 may include a duplexer or a multiplexed connection to the sample module 235 in the event that a single coil serves as both transmitter and receiver in the sample module 235. If the transmitter and receiver are separate coils in the sample module 235, then the Tx/Rx module 225 only includes two connections, one to each coil of the sample module 235. Alternatively, more connections may be used if advantageous for the operation of the NMR device 20.

The Tx/Rx module 225 may also include impedance matching circuits to match the impedance of the receiver coil in the sample module 235 to the amplification electronics in the Tx/Rx module 225. The Tx/Rx module 225 may also include impedance matching and transmit pulse amplification electronics to match the impedance of the transmitter coil in the sample module 235.

The Tx/Rx module 225 may also include connections to the RF control module 240 and at least two configuration choices are available for such connections. First, if Tx/Rx module 225 routes analog signals to and from RF control module 240, the connections between the Tx/Rx module 225 and the RF control module 240 are all that are required. Second, the RF control module 240 may transmit digital signals to the Tx/Rx module 225, in which case the connections are digital, and the Tx/Rx module 225 additionally includes analog-to-digital conversion circuits for NMR signals received from and sent to RF control module 240 and the Tx/Rx module 225 also includes digital-to-analog conversion circuits for pulse sequence signals received from RF control module 240.

The sample module 235 is configured to interrogate the sample fluid. The sample module 235 may also be referred to as an RF probe in an NMR device or system. In one embodiment, the sample module 235 comprises a magnetic field detector, for example a receiver coil that is configured to detect the RF magnetic field NMR signals from the sample during a measurement. The sample module 235 may also include a magnetic field transmitter, for example an excitation coil, that is configured to transmit a magnetic field stimulus to the sample. In one embodiment, the magnetic field detector (i.e., receiver coil) and the magnetic field transmitter (i.e., excitation coil) may be integrated into the same physical device (e.g., a single coil). In an alternative embodiment, the magnetic field detector (i.e., receiver coil) and the magnetic field transmitter (i.e., excitation coil) may be separate physical devices.

In operation, the Tx/Rx module 225 applies a current to the excitation coil of the sample module 235, which in turn generates a stimulus magnetic field that is directed to the sample. In one embodiment, the Tx/Rx module 225 applies current in a sequence of pulses and the sample module 235 in turn generates a sequence of stimulus magnetic field pulses. In response to the stimulus magnetic field, the target element in the sample emits a responsive magnetic field at a frequency characteristic of the NMR properties of the target element. The receiver coil in the sample module 235 detects the responsive magnetic field from the target element and generates a voltage that is sensed by the Tx/Rx module 225. The Tx/Rx module 225 in turn generates an electrical signal that corresponds to sensed voltage and therefore also corresponds to the target element.

The sample module 235 may also optionally include an electrical tuning circuit element that is configured to tune the magnetic field detector and/or the magnetic field transmitter to a desired RF frequency. In one embodiment, the desired frequency is received from the Tx/Rx module 225 or alternatively received from the RF control module 240. In an embodiment where the sample module 235 is to be operated in an untuned (e.g., broadband) mode, the electrical tuning circuit element may be omitted. Advantageously, the electrical tuning circuit may alternatively be included in the Tx/Rx module 225.

The sample module 235 may also optionally include mechanical hardware to physically guide and/or hold and/or confine the sample I/O module 205 inside the sample module 235. Such hardware may optionally include a tube or conduit guide, with or without a mechanical stop to ensure that the sample rests reproducibly in the same position in the sample module 235. Such mechanical hardware also ensures that the sample module 235 remains rigid with respect to magnet module 215.

The RF control module 240 is configured to provide programmable synthesis of the transmitted RF pulse trains and data acquisition of the resulting NMR signals, as well as subsequent signal processing and analysis. In one embodiment, the RF control module 240 uses programmable controls—microprocessors, field programmable gate arrays, and similar integrated circuits—to control the overall operation of the NMR device 20. The RF control module 240 sets the RF frequency based on the target element whose concentration is to be measured, as determined by the element's gyromagnetic ratio. In one embodiment, the RF control module 240 sends a desired transmit frequency and a desired receive frequency to the Tx/Rx module 225. In an alternative embodiment, the RF control module 240 sends a desired transmit frequency and a desired receive frequency to the sample module 235. The RF control module 240 comprises software or firmware modules embedded in the programmable circuits and these software or firmware modules are configured to control the operation of the NMR device 20. For example, an RF synthesizer software module may be configured to calculate the RF frequency waveforms and generate them digitally. Additionally, a pulse synthesizer software module may be configured to calculate the train of excitation pulses required to perform, for example, a concentration measurement.

In one embodiment for multiple element characterization, using broadband or switchable-narrowband electronics, separate calculations of frequency values may be made for each element. Advantageously, information derived from measurements made at the frequency of one or more elements may be used to determine the frequencies appropriate for further elements.

The RF control module 240 contains connections to the Tx/Rx module 225. In some implementations of RF control module 240, the module includes digital-to-analog converters to convert the excitation pulse train to an analog voltage to be applied directly to the sample module 235, as well as analog-to-digital converters to convert the analog NMR signal stream into digital form for storage in memory 25 and subsequent processing. In other embodiments, such conversion electronics may be integrated with the Tx/Rx module 225.

The RF control module 240 programmable electronics may also comprise embedded software or firmware modules to process the acquired NMR signals. Such embedded software or firmware modules may be configured to provide diagnostic analyses to ensure that the NMR device 20 is operating properly. Such embedded software or firmware modules may be configured to evaluate of the NMR signals, for example a train of echo signals from a CPMG experiment, and may also be configured to evaluate the number of nuclei producing the signal, and thereby determine the concentration of the element being measured.

The main control module 250 is configured to control overall system operation and electric power distribution to the other modules. In one embodiment, the main controller module 250 routes utilities such as conditioned electric power, common timing (clock) signals, and the like to the other modules in the NMR device 20. In operation, the main controller module 250 is configured to synthesize the appropriate NMR frequency waveforms and initiate pulse sequences used to excite the sample. The main control module 250 is also configured to control acquisition of the NMR signals, in the form of a train of echoes emitted from the sample (e.g., between the applied pulse sequences) in response to the pulse sequences. The main control module 250 is also configured to process the acquired NMR signals and validate operation of the NMR device 20 and determine the elemental concentration in the sample based on an analysis of the acquired NMR signals.

The human I/O module 260 is configured to receive various forms of input from an operator regarding the operation and diagnostics of NMR device 20. For example, the human I/O module 260 may receive certain parameters and instructions from an operator. The human I/O module 260 is also configured to provide output. Output may be provided in a variety of forms such as data to electronic files or visual display devices, audio output and tactile output such as vibrations.

The human I/O module 260 is also configured to manage direct wired or wireless and indirect network connections to other devices, such as one or more peer NMR devices and one or more analytics servers (e.g., analytics server 40 in FIG. 1).

The power source module 270 is configured to provide power to the NMR device 20 either through a continuous power supply such as an electrical outlet or through a limited power supply such as a battery pack. Advantageously, various forms of limited power supplies allow the NMR device 20 to be portable. Alternatively, power may be supplied by a solar power module or other portable module capable of supplying power indefinitely.

Figure 3:
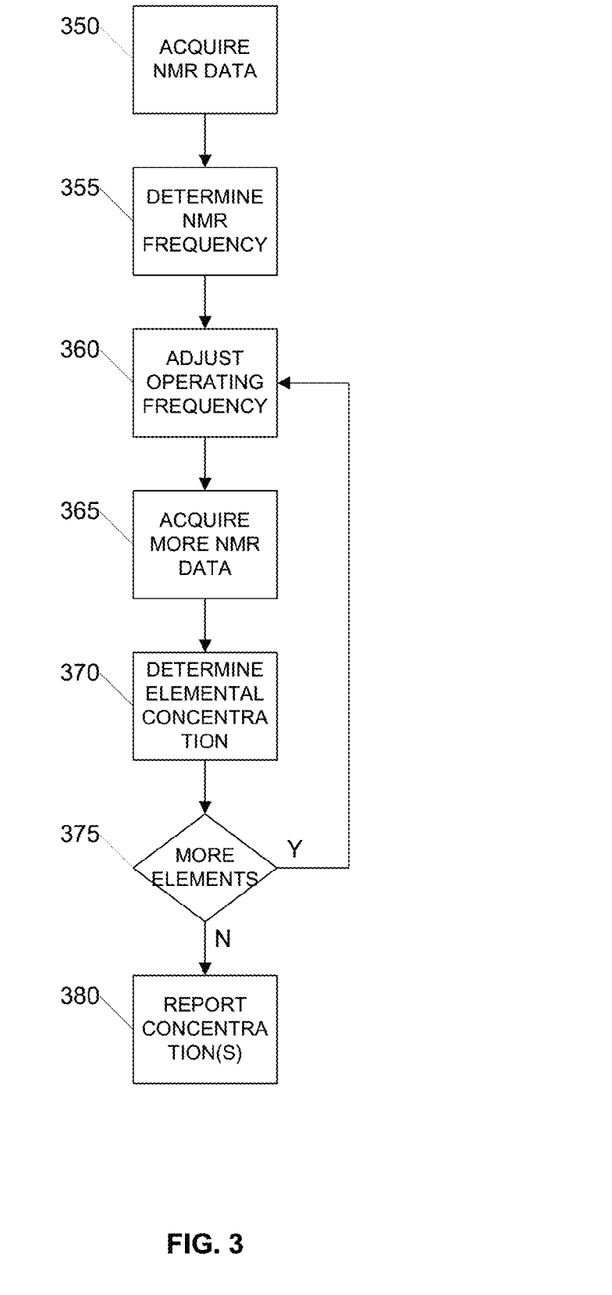
FIG. 3 is a flow diagram illustrating an example process for determining the concentration of an element in a fluid according to an embodiment of the invention.

FIG. 3 is a flow diagram illustrating an example process for determining the concentration of an element in a fluid according to an embodiment of the invention. In one embodiment, the illustrated process may be carried by the system 10 previously described in FIG. 1 or by an NMR device 20 such as previously described in FIG. 2. In one embodiment, the size of the NMR device 20 is substantially equal to or less than 0.5 cubic meters and the size of the sample is substantially equal to or less than 10 milliliters. In an alternative embodiment, the size of the NMR device 20 is substantially equal to or less than 0.03 cubic meters. Initially, in step 350, NMR data from a target chemical element is acquired and then analyzed in step 355 to determine the frequency of the NMR signal. For example, the frequency of the signal from the target element may be determined by subjecting the sample to pulses of a frequency that is substantially equal to the expected resonance frequency at which the target element in the sample is excited. Such pulses would therefore trigger emission of a signal from the sample at the NMR frequency for the target element.

Because the measured NMR frequency of a target chemical element changes over time in response to changes in the temperature of the magnet module, the device operating frequency, also called the spectrometer frequency, is adjusted based on the measured NMR frequency of the target element. Accordingly, in step 360, the operating frequency of the NMR device is adjusted to a value that is offset from the measured NMR frequency of the target element by a particular amount. Advantageously, the offset amount is determined such that subsequent NMR measurements for the target element are as precise as possible. Importantly, the determined value of the offset may differ from NMR device to NMR device and is therefore established during the process of manufacturing each device. The optimal offset frequency for a given NMR device may be determined by performing a single measurement or a series of measurements during which the spectrometer frequency is stepped through a range of frequencies. For each measurement, the signal strength, spectrometer frequency, and measured NMR frequency are recorded. A plot of signal strength versus the difference between the spectrometer and measured NMR frequencies (that is, the offset frequency) may be used to select an offset frequency that maximizes signal and/or has other advantageous properties. If the concentration of a target chemical element other than the element used for the current NMR frequency determination is to be determined, the frequency adjustment algorithm takes into account the known ratiometric relationships between the expected NMR frequencies for the elements involved, using parameter values and methods well known in the art. These known relationships are then used to determine the operating frequency for the target chemical element.

After the operating frequency for the target element has been set in step 360, more NMR data is acquired from the target element in the sample as shown in step 365. This additional NMR data is then analyzed in step 370 to determine and store in memory the concentration of the target element in the sample. If the NMR device is operating to determine and store in memory the concentrations of plural target elements, as determined in step 375, the process proceeds by returning to step 360 where a new adjustment is made to the operating frequency, appropriate to the new target element. Advantageously, the information from the initial NMR frequency determination in step 355 may be used for this new frequency adjustment step 360.

Once all of the plural target elements have been measured (or the single target element has been measured), the resulting concentrations may be reported as shown in step 380, for example by storing the results in memory on the NMR device and/or providing the results to the user via the human I/O module. The results may also be provided to other devices, for example the analytics server 40 described in FIG. 1.

Figure 4:
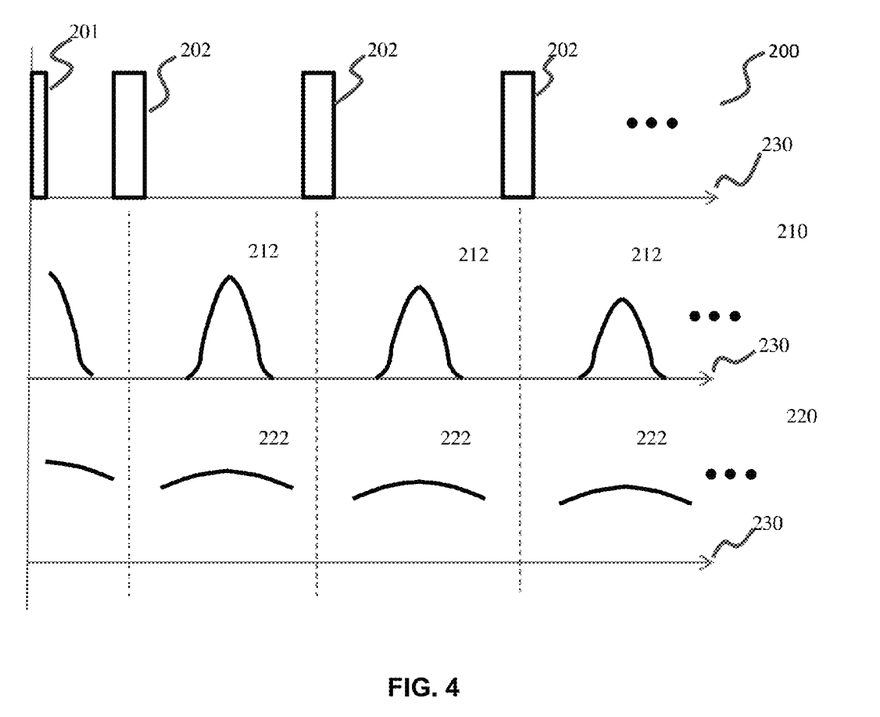
FIG. 4 is a graph diagram illustrating an example nuclear magnetic resonance Carr-Purcell-Meiboom-Gill ("CPMG") pulse sequence signal train according to an embodiment of the invention.

FIG. 4 is a diagram illustrating an NMR CPMG pulse sequence 200 and echo signal trains 210, 220 according to an embodiment of the invention. Only the first portions of a typical excitation and signal trace are shown; in a typical measurement hundreds or thousands of pulses and echoes are involved. The upper trace 200 shows the envelope of the excitation pulse sequence. The first pulse 201 excites the nuclear magnetic moments into a coherent response that decoheres over time, due to slight differences in the field experienced by each nucleus. Subsequent "refocusing" pulses 202 re-establish signal coherence. The second trace 210 shows an example of an envelope of NMR echo signals 212 emitted as the nuclear magnetic moments precess around their equilibrium orientation. Traces 200, 210, and 220 all share the same time axis 230, and in all cases, the radio frequency of the excitation and response signals is very high, compared to the time scale of the pulse lengths, and only the amplitude envelope is shown. Trace 210 depicts the signals 212 that would be observed for example, when the magnet module produces a comparatively inhomogeneous magnetic field across the sample. Trace 220 depicts the situation when the magnetic field is more homogeneous. Alternatively, trace 220 depicts what might be observed when the refocusing pulses 202 of the CPMG sequence are placed close together in time. Echo data 222 of the form 220 may be preferred since they have the advantage that NMR signals are acquired at all times between the RF pulses 202; in contrast, data of the form of trace 210 have a significant fraction of time with no NMR signals present.

Figure 5A:
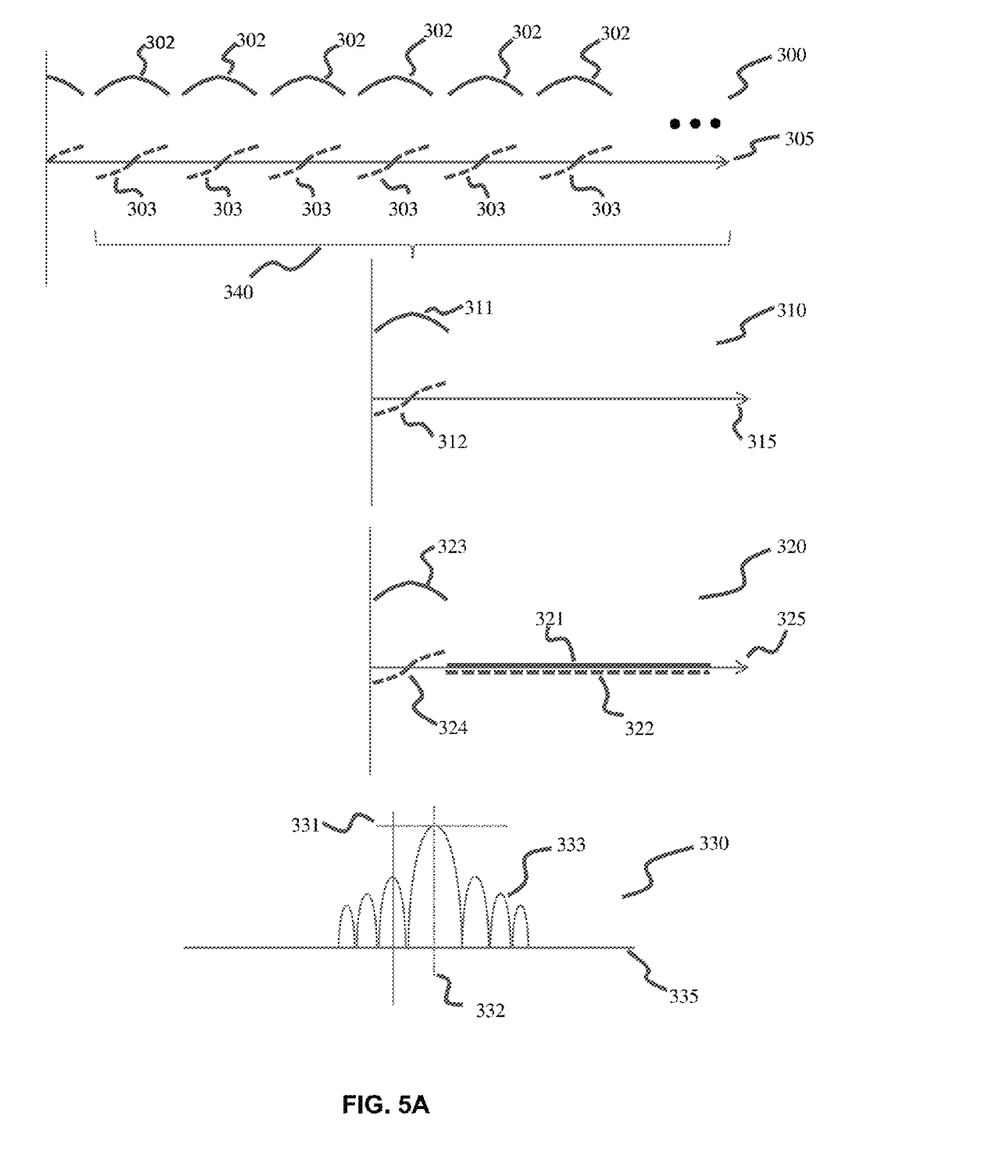
FIGS. 5A and 5B are graph diagrams illustrating an example data analysis according to an embodiment of the invention.

The amplitude of the detected signal contains the information needed to determine the concentration of the target element. The signal amplitude may be determined in a number of ways. FIG. 5A presents one embodiment, beginning with data of the form 220 of FIG. 4. In FIG. 5, this data is shown in trace 300 in the form of a two-channel demodulation of the NMR signal from the sample module, a data depiction that is standard in the art. The signals 302 may be considered the real parts of the complex-valued CPMG echo signals, while the signals 303, coincident in time with signals 302, may be considered the imaginary parts of the complex-valued CPMG echo signals. The signals depicted in trace 300 occur while the time 305 elapses. The data analysis proceeds by averaging together (step 340) the signals comprising each echo. This averaged echo data set is shown in trace 310, where the averaged real part (311) and imaginary part (312) are plotted against a new time axis 315. This data is then zero-filled (extended in time by adding data points equal to zero) to a substantial degree so that the data set is extended 4-fold or 8-fold or more in length, as shown in trace 320, where the zero filling for the real part of the averaged-echo data is shown as line 321 and the imaginary part as line 322. The new time axis 325 is similar to the previous axis 315. Then the zero-filled data set of trace 320 is subjected to a complex-valued Fourier Transformation. The magnitude of the resulting NMR spectrum 330 is then analyzed to determine the magnitude 331 of the maximum signal (the NMR peak). It may also be advantageous to extract the frequency 332 at which the NMR peak occurs along the frequency axis 335. The magnitude 331 is proportional to the number of nuclei producing the CPMG signals 302 and 303 so it can be used to determine the concentration of the element in question via a calibration procedure described below. The frequency value 332 may be used to adjust the device operating frequency, it may be used to monitor the status of the device, it may be used as part of further data analysis, or it may have other uses.

Figure 5B:
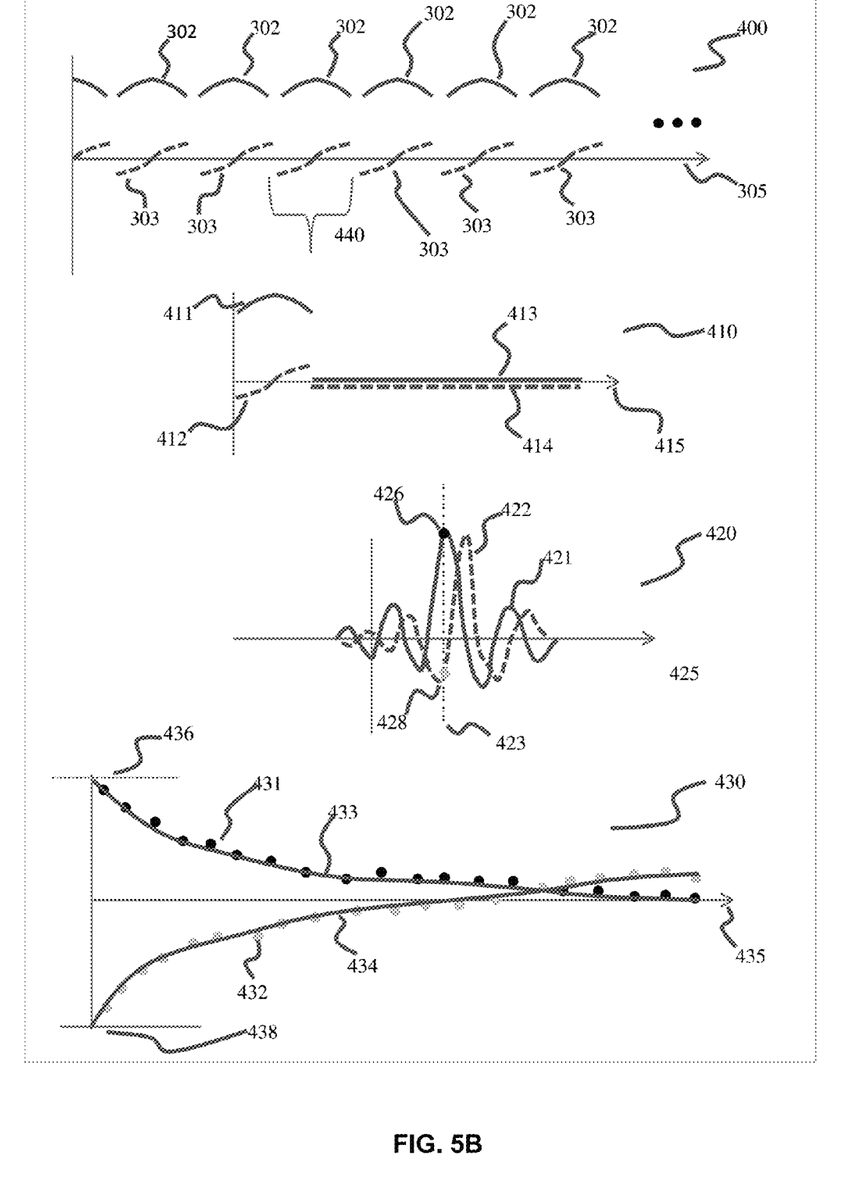

FIG. 5B shows another embodiment of the data analysis process that contains more steps and that may prove advantageous in improving the accuracy of the concentration values determined by the device. After first carrying out the steps described for FIG. 5A, the data are further analyzed by returning to the original data 400, which is the same as the data 300 shown in FIG. 5A. The next step in the extended process is to treat each of the echo data pairs 302, 303 separately from the other echo pairs 302, 303. Each single signal echo pair is extracted 440 from the full data set 400 and zero-filled as described in FIG. 5A. The resulting data are shown in trace 410, where the real part 411 and the imaginary part 412 of the single echo are shown with their zero-filled points 413 and 414, respectively, all plotted against a time axis 415. As described in FIG. 5A, the data 410 are subjected to a complex Fourier Transform, the complex output of which is shown in trace 420. Here, in contrast to trace 330 in FIG. 5A, the real 421 and imaginary 422 parts of the Fourier Transform output are shown, plotted against a frequency axis 425. Now, the frequency of the NMR peak 332 as determined from trace 330 in FIG. 5A is used to pick off two values from trace 420; the value 426 of the real part 421 evaluated at the NMR frequency 332 (shown in 420 as dotted line 423) and the value 428 of the imaginary part 422 evaluated at the NMR frequency 332 (423). The points 426 and 428 can be taken to define the complex-valued amplitude of the detected NMR signal for each echo 302, 303 individually. Two such points can be determined for each of the echo signals in trace 400, and the time of the occurrence of the echo in question in trace 400 can be associated with the two points. The full collection of pairs of points 426, 428 can be plotted versus the times associated with each pair 435, producing a signal decay curve 430. The set 431 of points 426, and the set 432 of points 428 may be independently analyzed so that each set can be used to extrapolate (lines 433 and 434) the trend of the data backward in time, i.e., to the left on the plot 430. The extrapolations 433 and 434 may be achieved by any of a number of means, including least-squares fitting of a functional form to the data, direct calculation of parameters from the values of the data points, or other methods known in the art. The extrapolations 433 and 434 may be completely independent or they may contain linked or common parameters. The intersections 436, 438 of the extrapolations with the vertical axis, defining time equaling zero, may be taken as the complex-valued zero time amplitude of the NMR signal. The overall NMR signal strength, which is proportional to the number of nuclei contributing to the signal shown in trace 400, can be calculated as the complex absolute magnitude of the points 436, 438.

Alternatively, the time domain data set (i.e., trace 400 in FIG. 5B or trace 210 or trace 220 in FIG. 4) may be evaluated at the location of each echo to determine the echo amplitude, or the time domain data set can be fit with a mathematical function that is adjusted to fit the data points near the location of each echo, with the resulting fitting function used to determine the amplitude of each echo. No matter the method used to determine the real-valued or complex-valued amplitude of each echo, the values determined may be plotted as a function of echo number (or experimental time) to form an echo decay curve, which may be complex-valued.

The NMR signal amplitude is proportional to the concentration of the detected element. Converting it into an absolute concentration requires measurement of a calibration sample of known concentration. The process of determining the numbers needed to calibrate the device may be very similar to, or the same as, the measurement methods described above. Once the NMR signal strength has been measured for the calibration sample, the ratio between the concentration and the NMR signal strength can be determined. For subsequent measurements of unknown samples, the NMR signal strength measured for the unknown sample can be multiplied by the ratio determined during calibration to yield the concentration of the unknown sample.

Figure 6:
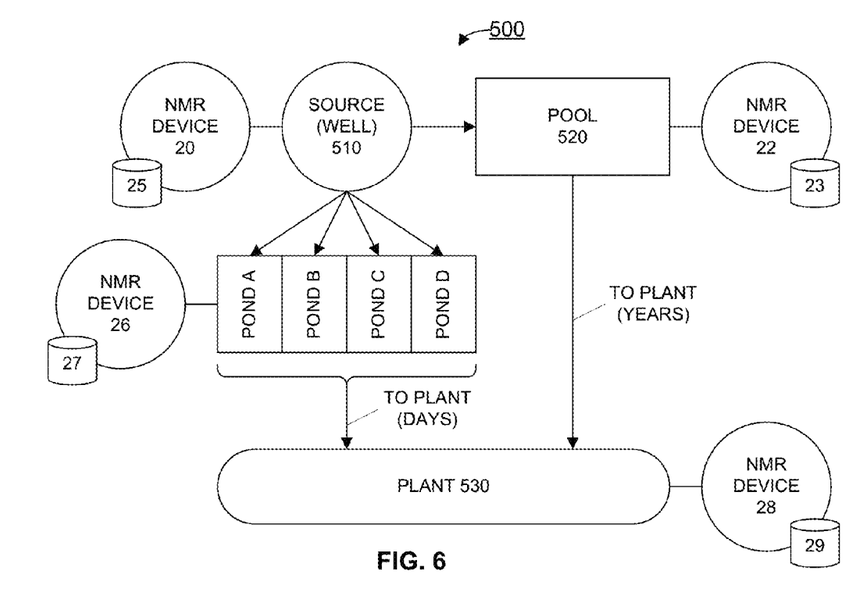
FIG. 6 is a block diagram illustrating an example mining operation incorporating high precision elemental composition determination using a nuclear magnetic resonance device according to an embodiment of the invention.

FIG. 6 is a block diagram illustrating an example mining operation 500 incorporating high precision elemental composition determination using one or more nuclear magnetic resonance devices 20, 22, 26 and 28 according to an embodiment of the invention. In the illustrated embodiment, the operation 500 comprises a source 510, a pool 520 and a plant 530. The operation 500 also includes a plurality of ponds A, B, C and D for staging fluids from the source 510 before delivery to the plant 530. The geographic location of the source, ponds, pool and plant can be such that they are all co-located or such that some or all are remote from each other. As indicated, fluids from the ponds A-D are delivered to the plant in a matter of days while fluids from the pool 520 are delivered to the plant in a matter of years.

The NMR devices 20, 22, 26 and 28 are each associated with one of the areas of the operation 500 where fluids reside and/or are processed. NMR device 20 is associated with the source 510, NMR device 22 is associated with the pool 520, NMR device 26 is associated with the ponds A-D and NMR device 28 is associated with the plant 530. Notably, NMR device 26 may comprise a plurality of NMR devices, one for each pond. The various NMR devices can be communicatively coupled with each other by way of one or more wired or wireless networks. Although not shown, an analytics server may also be included in the operation 500.

In the illustrated example embodiment, the sample source 510 is located out in the field—remote from the processing plant 530. A portion of the sample from the source 510 is provided to NMR device 20 and the sample is interrogated in the field. The results of the sample interrogation may be initially analyzed by the NMR device 20 in the field or the results (and/or initial analysis) may be provided to an analytics server (not shown) for initial and/or further analysis. The results of the field analysis may then be used to control or influence the process by which the sample is collected from the source, e.g., by causing the source to drill deeper.

As shown in the illustrated example embodiment, a portion of the sample from the source 510 is provided to the pool 520 for longer term storage and/or processing and a portion is also provided to the various ponds A-D. Accordingly, NMR device 22 iteratively interrogates the sample in the pool 520 and NMR device 26 similarly iteratively interrogates the sample in the ponds A-D. Analysis of the results of the sample interrogation by NMR device 22 and NMR device 26 may take place at the respective NMR device or at one or more local or remote analytics servers. Advantageously, such analysis may influence or control the flow of the sample from the pool 520 or the ponds A-D to the plant 530.

At the plant 530, the sample is further processed and/or refined and may be singularly or iteratively interrogated by NMR device 28 at the plant 530. The results of the sample interrogation by NMR device 28 may be analyzed by the by NMR device 28 itself and/or one or more analytics servers. Further processing of the sample in the plant 530 may be influenced or controlled by the results of the analysis of the sample interrogation as previously discussed.

Figure 7:
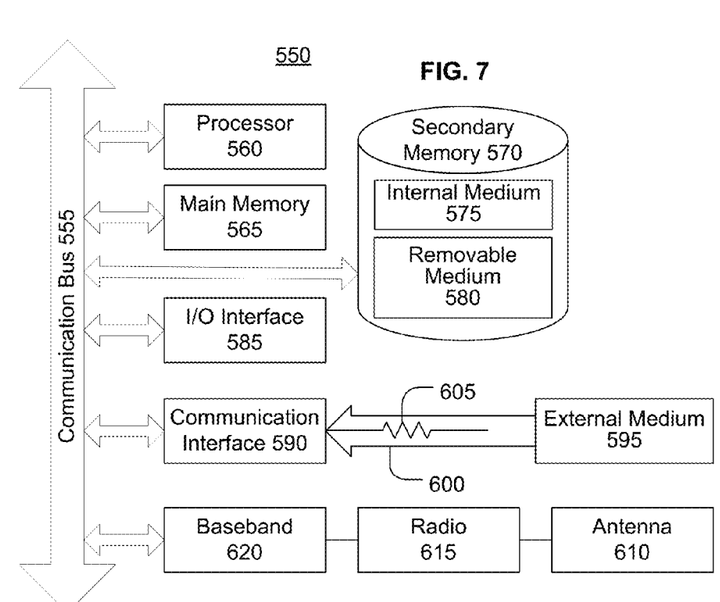
FIG. 7 is a block diagram illustrating an example wired or wireless processor enabled device that may be used in connection with various embodiments described herein.

FIG. 7 is a block diagram illustrating an example wired or wireless system 550 that may be used in connection with various embodiments described herein. For example, the system 550 may be used as or in conjunction with an NMR device 20, an analytics server 40 or a process device 50 such as previously described with respect to FIGS. 1, 2 and 6. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that were previously described with respect to FIGS. 2 and 3.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An apparatus, comprising:
   a non-transitory computer readable storage medium configured to store executable programmed modules and data;
   a processor communicatively coupled to the storage medium and configured to execute programmed modules stored therein;
   a magnet module configured to create a static magnetic field;
   a sample input/output module configured to support a test sample including an unknown concentration of a first target element in a location where the test sample is substantially exposed to the static magnetic field;
   a sample module configured to
     receive a first electrical current and produce a corresponding first stimulus magnetic field at a nuclear magnetic resonance (NMR) frequency of the first target element,
     expose the test sample to the first stimulus magnetic field,
     detect a first responsive magnetic field produced by the first target element in the test sample in response to the first stimulus magnetic field,
     generate a first voltage in response to the first responsive magnetic field produced by the first target element in the test sample, wherein the first voltage corresponds to the NMR frequency of the first target element,
   a transmit and receive module communicatively coupled to the sample module and configured to
     provide, in accordance with a transmit frequency, the first electrical current to the sample module, wherein the transmit frequency is determined based at least in part on the NMR frequency of the first target element, and
     detect, in accordance with a receive frequency, the first voltage generated by the sample module, wherein the receive frequency is determined based at least in part on the NMR frequency of the first target element, and
     generate a first electrical signal based on the first voltage, wherein the first electrical signal corresponds to the NMR frequency of the first target element, and wherein the first electrical signal comprises a first real part and a first imaginary part in a time domain;
   a radio frequency control module stored in the storage medium and configured to be executed by the processor, the radio frequency control module configured to adjust the transmit frequency and the receive frequency of the transmit and receive module; and
   a main control module stored in the storage medium and configured to be executed by the processor, the main control module configured to
     determine an average for the first real part and an average for the first imaginary part of the first electrical signal from the transmit and receive module, transform the averaged first real part and averaged first imaginary part of the first electrical signal from the time domain to a frequency domain, determine a first NMR peak amplitude of the first electrical signal based at least in part on the transformed averaged first real part and averaged first imaginary first part of the first electrical signal, determine the concentration of the first target element included in the test sample based at least in part on the first NMR peak amplitude of the first electrical signal and a predetermined ratio of a known concentration of the first target element and an amplitude of a second electrical signal associated with a calibration sample that includes the known concentration of the first target element, and store the concentration of the first target element included in the test sample in the storage medium.

2. The apparatus of claim 1, wherein the strength of the static magnetic field is substantially uniform throughout the test sample.

3. The apparatus of claim 2, wherein the uniformity of the strength of the static magnetic field is substantially one part in ten thousand.

4. The apparatus of claim 1, wherein the magnet module includes one of a permanent magnet, an electromagnet, or a superconducting magnet.

5. The apparatus of claim 4, wherein the magnet module excludes materials to stabilize the temperature of the one of a permanent magnet, an electromagnet, or a superconducting magnet.

6. The apparatus of claim 1, wherein the transmit and receive module is configured to provide the first electric current in pulses, and wherein the sample module is further configured to expose the test sample to the first stimulus magnetic field in pulses that correspond to the pulses of the first electrical current received from the transmit and receive module.

7. The apparatus of claim 1, wherein the first target element comprises a non-proton element, wherein the sample module is further configured to detect a relaxation magnetic field produced by the first target element in the test sample in response to the first stimulus magnetic field, wherein the first voltage corresponds to the NMR frequency of the non-proton element, and wherein the main control module is configured to determine a concentration of the non-proton element in the test sample.

8. The apparatus of claim 1, wherein the test sample includes a second target element, wherein:

the radio frequency control module is further configured to adjust the transmit frequency and the receive frequency of the transmit and receive module in accordance with a NMR frequency of the second target element, the sample module is further configured to receive a second electrical current and produce a corresponding second stimulus magnetic field at a NMR frequency of the second target element, expose the test sample to the second stimulus magnetic field, detect a second responsive magnetic field produced by the second target element in the test sample, and generate a second voltage in response to the second responsive magnetic field, the transmit and receive module is further configured to provide the second electrical current to the sample module in accordance to a transmit frequency determined based at least in part on the NMR frequency of the second target element, detect the second voltage generated by the sample module in accordance to a receive frequency determined based at least in part on the NMR frequency of the second target element, and generate a third electrical signal, wherein the third electrical signal comprises a second real part and a second imaginary part in the time domain, and the main control module is further configured to:

determine an average for the second real part and an average for the second imaginary part of the third electrical signal from the transmit and receive module;

transform the averaged second real part and averaged second imaginary part of the third electrical signal from the time domain to the frequency domain;

determine a second NMR peak amplitude of the third electrical signal based at least in part on the transformed averaged second real part and second imaginary part of the third electrical signal;

determine a concentration of the second target element in the test sample based at least in part on the second NMR peak amplitude of the third electrical signal and a predetermined ratio of a known concentration of the second target element and an amplitude of a fourth electrical signal associated with a calibration sample that includes the known concentration of the second target element; and store the concentration of the second target element in the storage medium.

9. The apparatus of claim 8, wherein the first target element comprises hydrogen and is present in a solvent of the test sample and the second target element is present in one of a solute, suspension, or precipitate of the test sample.

10. The apparatus of claim 1, wherein a size of the overall device is less than 0.5 cubic meters and a size of the test sample is less than 10 milliliters.

11. The apparatus of claim 1, wherein the first real part and the first imaginary part of the first electrical signal in the time domain includes a first echo data pair, wherein the first echo data pair comprises a portion of the first real part and a portion of the first imaginary part of the first electrical signal.

12. The apparatus of claim 11, wherein the main control module is further configured to transform the first echo data pair from the time domain to the frequency domain.

13. The apparatus of claim 12, wherein the main control module is further configured to determine an NMR peak frequency corresponding to the first NMR peak amplitude of the first electrical signal.

14. The apparatus of claim 13, wherein the main control module is further configured to:

determine a real value and an imaginary value associated with the transformed first echo data pair at the NMR peak frequency;

extrapolate the real value and the imaginary value associated with the transformed first echo data pair in the time domain; and determine a zero-time amplitude of the first electrical signal based at least in part on the extrapolated real value and imaginary value.

15. The apparatus of claim 14, wherein the zero-time amplitude comprises a complex value having a real and an imaginary component, wherein the main control module is further configured to determine an absolute magnitude of the zero-time amplitude of the first electrical signal, and wherein the concentration of the first target element included in the test sample is further determined based on the absolute magnitude of the zero-time amplitude of the first electrical signal.

16. A method, comprising:

generating a static magnetic field having substantially uniform strength;

receiving a test sample including an unknown concentration of a first target element, and supporting the test sample in a location where the test sample is substantially exposed to the static magnetic field;

generating a first stimulus magnetic field at a frequency substantially equal to a nuclear magnetic resonance (NMR) frequency of the first target element;

exposing the test sample to the first stimulus magnetic field;

detecting a first responsive magnetic field produced by the first target element in the test sample in response to the first stimulus magnetic field;

generating a first voltage in response to the first responsive magnetic field produced by the first target element in the test sample, wherein the first voltage corresponds to the NMR frequency of the first target element;

generating a first electrical signal based on the first voltage, wherein the first electrical signal corresponds to the NMR frequency of the first target element, and wherein the first electrical signal comprises a first real part and a first imaginary part in a time domain;

determining an average for the first real part and an average for the first imaginary part of the first electrical signal from the transmit and receive module;

transforming the averaged first real part and averaged first imaginary part of the first electrical signal from the time domain to a frequency domain;

determining a first NMR peak amplitude of the first electrical signal based at least in part on the transformed averaged first real part and averaged first imaginary part of the first electrical signal;

determining the concentration of the first target element included in the test sample based at least in part on the first NMR peak amplitude of the first electrical signal and a predetermined ratio of a known concentration of the first target element and an amplitude of a second electrical signal associated with a calibration sample that includes the known concentration of the first target element; and storing the concentration of the first target element included in the test sample in the storage medium.

17. The method of claim 16, further comprising controlling an extraction process or an enrichment process based at least in part on the concentration of the first target element in the test sample.

18. The method of claim 16, wherein the first real part and the first imaginary part of the first electrical signal in the time domain includes a first echo data pair, wherein the first echo data pair comprises a portion of the first real part and a portion of the first imaginary part of the first electrical signal.

19. The method of claim 18, further comprising:
transforming the first echo data pair from the time domain to the frequency domain;
determining an NMR peak frequency corresponding to the first NMR peak amplitude of the first electrical signal;
determining a real value and an imaginary value associated with the transformed first echo data pair at the NMR peak frequency;
extrapolating the real value and the imaginary value associated with the transformed first echo data pair in the time domain;
determining a zero-time amplitude of the first electrical signal based at least in part on the extrapolated real value and imaginary value, wherein the zero-time amplitude comprises a complex value having a real and an imaginary component; and determining an absolute magnitude of the zero-time amplitude of the first electrical signal, wherein the concentration of the first target element included in the test sample is further determined based on the absolute magnitude of the zero-time amplitude of the first electrical signal.

20. An apparatus, comprising:
a non-transitory computer readable storage medium configured to store executable programmed modules and data;
a processor communicatively coupled to the storage medium and configured to execute programmed modules stored therein;
a magnet module configured to create a static magnetic field;
a sample input/output module configured to support a test sample including an unknown concentration of a first target element in a location where the test sample is substantially exposed to the static magnetic field;
a sample module configured to
receive a first electrical current and produce a corresponding first stimulus magnetic field at a nuclear magnetic resonance (NMR) frequency of the first target element,
expose the test sample to the first stimulus magnetic field,
detect a first responsive magnetic field produced by the first target element in the test sample in response to the first stimulus magnetic field,
generate a first voltage in response to the first responsive magnetic field produced by the first target element in the test sample, wherein the first voltage corresponds to the NMR frequency of the first target element,
a transmit and receive module communicatively coupled to the sample module and configured to
provide, in accordance with a transmit frequency, the first electrical current to the sample module, wherein the transmit frequency is determined based at least in part on the NMR frequency of the first target element, and
detect, in accordance with a receive frequency, the first voltage generated by the sample module, wherein the receive frequency is determined based at least in part on the NMR frequency of the first target element, and
generate a first electrical signal based on the first voltage, wherein the first electrical signal corresponds to the NMR frequency of the first target element, and wherein the first electrical signal comprises a first real part and a first imaginary part in a time domain;
a radio frequency control module stored in the storage medium and configured to be executed by the processor, the radio frequency control module configured to adjust the transmit frequency and the receive frequency of the transmit and receive module; and
a main control module stored in the storage medium and configured to be executed by the processor, the main control module configured to
determine an average for the first real part and an average for the first imaginary part of the first electrical signal from the transmit and receive module, wherein the first real part and the first imaginary part of the first electrical signal in the time domain includes a first echo data pair, and wherein the first echo data pair comprises a portion of the first real part and a portion of the first imaginary part of the first electrical signal,
transform the averaged first real part and averaged first imaginary part of the first electrical signal from the time domain to a frequency domain, determine a first NMR peak amplitude of the first electrical signal based at least in part on the transformed averaged first real part and averaged first imaginary first part of the first electrical signal, transform the first echo data pair from the time domain to the frequency domain, determine an NMR peak frequency corresponding to the first NMR peak amplitude of the first electrical signal, determine a real value and an imaginary value associated with the transformed first echo data pair at the NMR peak frequency, extrapolate the real value and the imaginary value associated with the transformed first echo data pair in the time domain, determine a zero-time amplitude of the first electrical signal based at least in part on the extrapolated real value and imaginary value, wherein the zero-time amplitude comprises a complex value having a real and an imaginary component, determine an absolute magnitude of the zero-time amplitude of the first electrical signal, wherein the concentration of the first target element included in the test sample is further determined based on the absolute magnitude of the zero-time amplitude of the first electrical signal, determine the concentration of the first target element included in the test sample based at least in part on the first NMR peak amplitude of the first electrical signal, the absolute magnitude of the zero-time amplitude of the first electrical signal, and a predetermined ratio of a known concentration of the first target element and an amplitude of a second electrical signal associated with a calibration sample that includes the known concentration of the first target element, and store the concentration of the first target element included in the test sample in the storage medium.

\* \* \* \* \*